United States Patent [19]
Henderson et al.

[11] Patent Number: 5,431,712
[45] Date of Patent: Jul. 11, 1995

[54] RECONFIGURABLE PNEUMATIC CONTROL FOR SPLIT/SPLITLESS INJECTION

[75] Inventors: Robert C. Henderson, Avondale; W. Dale Snyder, West Chester, both of Pa.

[73] Assignee: Hewlett-Packard Company, Palo Alto, Calif.

[21] Appl. No.: 251,830

[22] Filed: May 31, 1994

[51] Int. Cl.[6] .............................................. B01D 15/08
[52] U.S. Cl. .......................................... 95/22; 95/23; 95/82; 96/102; 96/103; 96/105
[58] Field of Search ................... 95/19, 22, 23, 82, 89; 96/101–103, 105

[56] References Cited

U.S. PATENT DOCUMENTS

| | | | |
|---|---|---|---|
| 4,948,389 | 8/1990 | Klein et al. | 96/102 X |
| 4,994,096 | 2/1991 | Klein et al. | 55/20 |
| 5,108,466 | 4/1992 | Klein et al. | 55/20 |
| 5,141,534 | 8/1992 | Sacks et al. | 96/102 |
| 5,163,979 | 11/1992 | Patrick et al. | 95/19 |

FOREIGN PATENT DOCUMENTS 1214627 12/1970 United Kingdom ................... 96/102

OTHER PUBLICATIONS

"Improving Splitless Injection with Electronic Pressure Programming," Philip L. Wylie, Richard J. Phillips, Kenneth J. Klein, Michael Q. Thompson, Bruce W. Hermann, pp. 649–655, *Journal of High Resolution Chromatography*, vol. 14, Oct. 1991.
"Optimization of GC Detector Parameters Using Electronic Pressure Control," Kenneth J. Klein, Paul A. Larson, Jill A. Brekenridge, pp. 616–619, *Journal of High Resolution Chromatography*, vol. 15, Sep. 1992.
"Applications of Auxiliary Electronic Pressure Control in Gas Chromatography," S. S. Stafford, K. J. Klein, P. A. Larson, R. L. Firor, V. Giarrocco, J. J. Sullivan, J. A. Brekenridge, Application Note-228-202, Sep. 1992, Hewlett Packard.
"Improving the sensitivity of your GC/MS system with electronic pressure control," Linda Doherty, MS Application Brief MS-92-5, Sep. 1992, Hewlett Packard.
"Gas Savings with Electronic Pressure Control," S. S. Stafford, K. J. Klein, P. A. Larson, Application Note 228-203, Sep. 1992, Hewlett Packard.
"Electronic Pressure Control (EPC) Bibliography," Hewlett-Packard Company, Nov. 1993.
"Applications of Electronic Pressure Control and Pressure Programming in Capillary Gas Chromatography," S. S. Stafford, K. J. Klein, P. A. Larson, R. L. Firor, P. L. Wylie, Application Note 228-141, Oct. 1991, Hewlett Packard.
"Gas Chromatography GC-17A User's Manual," Shimadzu Corporation, Chromatographic Instruments Division, chapters 9–11, 1992.

*Primary Examiner*—Robert Spitzer
*Attorney, Agent, or Firm*—Mark Z. Dudley

[57] ABSTRACT

Chromatographic system includes a split/splitless injection port operatively connected to an inlet line for receiving the regulated carrier gas flow, a separation column for receiving at least a portion of the mixture as a column flow, and a split vent line and a septum purge line for outputting respectively a split flow and a septum purge flow. A forward device driver operatively connected to a respective fluid controller controls fluid flow in the inlet line and a back device driver operatively connected to a respective fluid controller controls fluid pressure in the split line. A setpoint controller provides first and second setpoint control output values to a configuration module, which selectably configures the provision of each of the first and second setpoint control output values to a selected one of the forward and back device drivers according to the selection of a split or splitless injection mode.

10 Claims, 11 Drawing Sheets

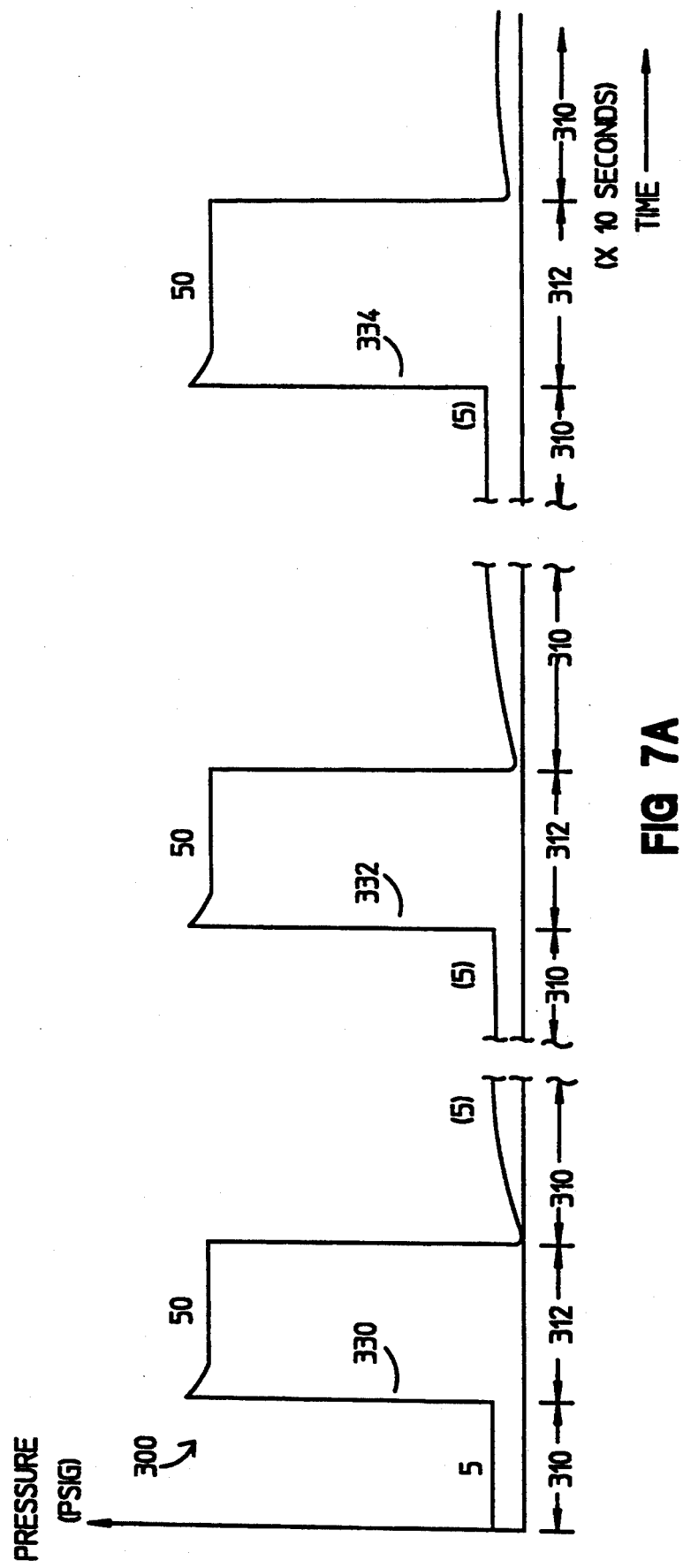

ical sample components. The basic mechanism underlying chromatographic analysis is the separation of a sample chemical mixture into individual components by injecting the sample into a carrier fluid (preferably a carrier gas) and transporting the mixture through a specially prepared separation column.
RECONFIGURABLE PNEUMATIC CONTROL FOR SPLIT/SPLITLESS INJECTION

FIELD OF THE INVENTION

The present invention relates to chromatographic analysis systems and, more particularly, to an apparatus and method for control of the fluid flow through a chromatographic analysis system that operates in split/splitless injection mode configurations.

BACKGROUND OF THE INVENTION

In analytical chemistry, gas chromatographic techniques have become important tools in the identification of chemical sample components. The basic mechanism underlying chromatographic analysis is the separation of a sample chemical mixture into individual components by injecting the sample into a carrier fluid (preferably a carrier gas) and transporting the mixture through a specially prepared separation column.

Precise control of the carrier gas flow is essential for maintaining the stability of the analyte retention times and for the accuracy of the quantitation of the analyte. Electronic pressure control (EPC) systems are known to offer programmed control of fluid pressures in response to sense signals from one or more sensors. An example of a modern electronic pressure control system is disclosed, for example, in Klein, et al., U.S. Pat. No. 4,994,096 and U.S. Pat. No. 5,108,466, the disclosures of which are incorporated herein by reference. Klein et al. also disclose electronic pressure control of fluids in "CGC Using a Programmable Electronic Pressure Controller,"*J. High Resolution Chromatography* 13:361, May 1990.

A conventional gas chromatographic system may be constructed to include a particular type of injection port known as a split/splitless inlet capable of operation in either of two injection modes. FIG. 1 shows the flow paths of the carrier gas flow during a splitless injection; FIG. 2 shows the flow paths of the carrier gas flow during split injection modes. As shown in FIG. 1, carrier gas is passed through a flow controller (14) to the split/splitless injection port (12) where the injected sample mixes with the carrier gas and the mixture is directed into a separation column (18). The carrier gas flow also passes to the septum purge line (12A) while any non-analyzed mixture flow is blocked in a split line (12B) by setting a three-way valve (20) to block split flow. Alternatively, as shown in FIG. 2, the three-way valve (20) can be set to pass split vent gas flow through a split vent line (12C) to a pressure controller (24) and a split vent (25), while the septum purge flow is passed to a septum purge flow controller (21) and a septum purge vent (22).

Typically, the temperature of the column (18) is controlled according to known techniques so that the sample will separate into its components. As the carrier gas (containing the sample) exits the column (18), the presence of one or more sample constituent components is detected by a detector (not shown). The pressure of the carrier gas entering the injection port (12) is controlled by the pressure controller (24) in response to an appropriate control signal.

Certain pressure programming techniques may be used to optimize the sample separation according to the injection mode employed. In particular, the split/splitless inlet is typically operated in split or splitless injection modes with control of the column flow effected by back pressure regulation. As shown in FIG. 1, in a splitless injection mode, the inlet (12) is first configured such that only a portion of the carrier gas that enters the inlet (12) can also enter the column (18), while the remainder "sweeps" the top of the inlet (12) and exits through the septum purge line (12A). The purge control valve (20) must be set so that the carrier gas that enters the inlet liner (12L) can only exit the split/splitless inlet into the column (18). While the purge gas continues to sweep the top of the inlet (12) and passes through the septum purge line (12A), the sample may be injected into the inlet liner (12L) and vaporized. Under ideal conditions, the vaporized sample is expected to transfer to the column during an initial "hold time" (typically 30 to 90 seconds). At the end of the splitless period, the purge valve (20) is opened (as shown in FIG. 2), and any residual carrier gas/sample mixture remaining in the inlet liner (12L) is swept out through the split vent line (12B).

As shown in FIG. 2, when the inlet (12) is operated in split mode, only a portion of the carrier gas that enters the inlet will also enter the column (18). Upon injection, a portion of the sample to be analyzed is carried into the column (18) while the remainder of the sample is split and directed out through the split line (12B) to the split vent line (12C) and the vent (25). The back pressure of the carrier gas exiting the injection port (12) is controlled by the pressure controller (24) in response to an appropriate control signal.

More detailed discussion of split/splitless injection techniques can be found in the prior art, such as in M. S. Klee, *GC Inlets—An Introduction*, Hewlett-Packard Company, February 1990; K. Grob, *Classical Split and Spritless Injection in Capillary GC*, 2nd Edition, Huethig, 1988; P. L. Wylie, J. Phillips, K. J. Klein, M. Q. Thompson, and B. W. Hermann, "Improving Splitless Injection with Electronic Pressure Programming,: *J High Resolution Chromatography* 14:649, October 1991; S. S. Stafford, K. J. Klein, P. A. Larson, F. L. Firor, and P. L. Wylie, "Applications of Electronic Pressure Control and Pressure Programming in Capillary Gas Chromatography, "Hewlett-Packard Company, Application Note 228-141, Publication Number (43) 5091-2731E, October 1991.

In splitless injection, sample transfer from the inlet liner (12L) to the separation column (18) is not wholly effective unless the entire sample is vaporized rapidly and uniformly into a vapor cloud that is available in the inlet liner (12L) during the hold time. Splitless injection is hampered when the sample is not sufficiently vaporized, or if sample components are lost when the most volatile components of the sample vaporize rapidly, expand to fill the liner (12L), and are swept away. This phenomena (known as sample discrimination) is worsened when working quantitatively with sensitive analytes, wide boiling range mixtures, or when increasing the sample volume for greater sensitivity.

In particular, a "high-flow" splitless injection (wherein the carrier gas entering the inlet is maintained at a high flow rate, and both the septum purge line and the split vent line are active) causes the flow over the top of the inlet to attract some of the sample into the purge line, with an undesireable loss of sample from the column, and a lowered total area count. A lower total flow rate would lessen this phenomena, but such a flow rate is impractical for effecting capillary separation because the purge flow is insufficient and the operation of the pressure controller (24) is problematic.

A technique exists for reconcentrating the vapor cloud into a narrow band at the head of the column before chromatography begins, such that the vapor expansion volume and flow rate onto the column are controlled by altering the inlet pressure. The pressure program is set to effect a "pressure pulse" whereby the column head pressure is increased prior to injection, then rapidly reduced to a setpoint best suited for column flow. However, in conventional split/splitless inlets, the time required to increase the pressure during such transitions is more than desireable, and the column head pressure does not increase (i.e., "pulse") as rapidly and effectively as desired. Sample discrimination can result.

Moreover, the combination of a three-way valve (20) and its associated drive circuitry contributes to the greater parts count and the increased cost of a split/splitless inlet. Three-way valves are also not as reliable as would be desired.

Accordingly, a need exists for a chromatographic system that is operable in split/splitless injection modes, wherein the carrier fluid flow is more accurately and reliably controlled, to afford an increased total area count, with use of a simpler and less expensive arrangement of components.

SUMMARY OF THE INVENTION

A preferred embodiment of a chromatographic system constructed according to our invention includes an injection port having an inlet therein for combining the sample and an inlet fluid to provide a column fluid flow to a separation column. The injection port includes an inlet line, a split line, and a septum purge line for passing respectively an inlet fluid flow, a split fluid flow, and a septum purge flow. Sensors provide sense information representative of the fluid flow in the inlet line and the column head pressure. A system controller determines control table information representative of a selected one of split and splitless injection modes and a selected one of forward and back pressure regulation modes. A first fluid controller, operatively connected to the inlet line, controls inlet fluid flow, and a second fluid controller, operatively connected to the split line, controls the column head pressure. A reconfigurable fluid control system determines first and second setpoint control output values, in accordance with the sense information and the control table information. The reconfigurable fluid control system then effects forward pressure regulation via first and second controllers according to the first and second setpoint control output values, respectively, when the injection port is operated in a split injection mode. The reconfigurable fluid control system is reconfigured to effect back pressure regulation via the second and first fluid controllers according to the first and second setpoint control output values, respectively, when the injection port is operated in a splitless injection mode.

The preferred embodiments of the contemplated gas chromatographic analysis system accomplish more accurate and repeatable control of the column fluid flow during transitions between split and splitless modes, and during operation in the splitless mode.

BRIEF DESCRIPTION OF THE DRAWINGS

FIGS. 7A and 7B are graphical representations of the column head pressure and inlet carrier gas flow, respectively, in the particularly preferred embodiment of FIG. 5, during alternating split and splitless injection modes, illustrating improved forward pressure control of the column head pressure.

DETAILED DESCRIPTION OF THE PREFERRED EMBODIMENTS

The apparatus and methods of the present invention may be employed to improve the control of the flow of a variety of compressible fluids in an analytical chromatographic system. Such fluids are intended to include gases, liquids, multiple component gases and liquids, and mixtures thereof capable of regulated flow. Gases are the preferred fluids according to the practice of the present invention, and therefore the following description of the invention will be directed to a gas chromatographic analytical system. Further, the description herein is directed to certain pneumatic characteristics of the fluid flow, such as pressure. The carrier gas may comprise one or more component gases (such as hydrogen, nitrogen, argon, methane, or helium) depending upon the particular chromatographic separation to be performed. However, it should be understood that the teachings herein are applicable to other fluids.

Figure 4A:
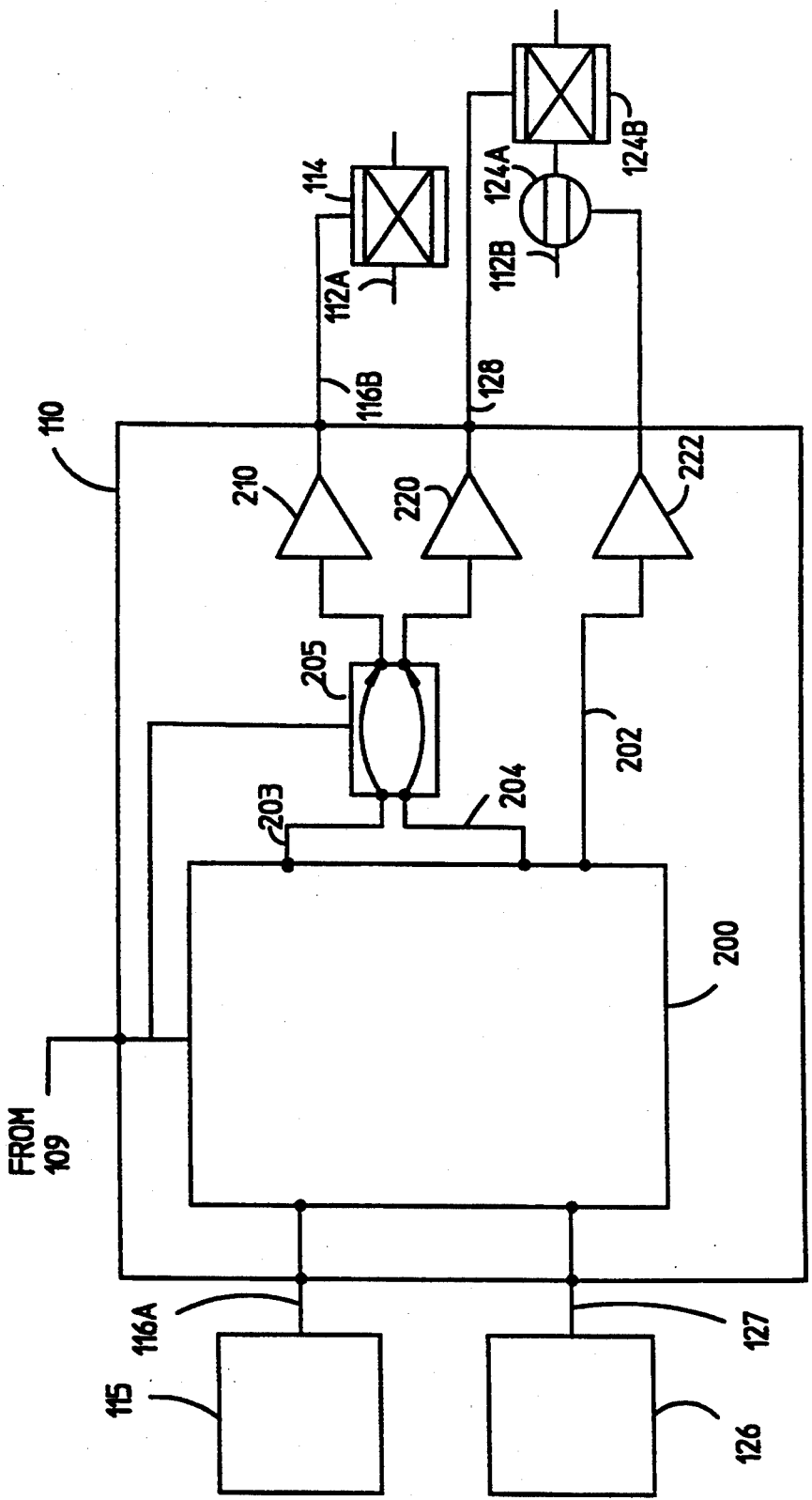
FIG. 4A is a simplified schematic representation of the preferred embodiment of FIG. 3, during operation in a first mode preferred for split injection.
Figure 4B:
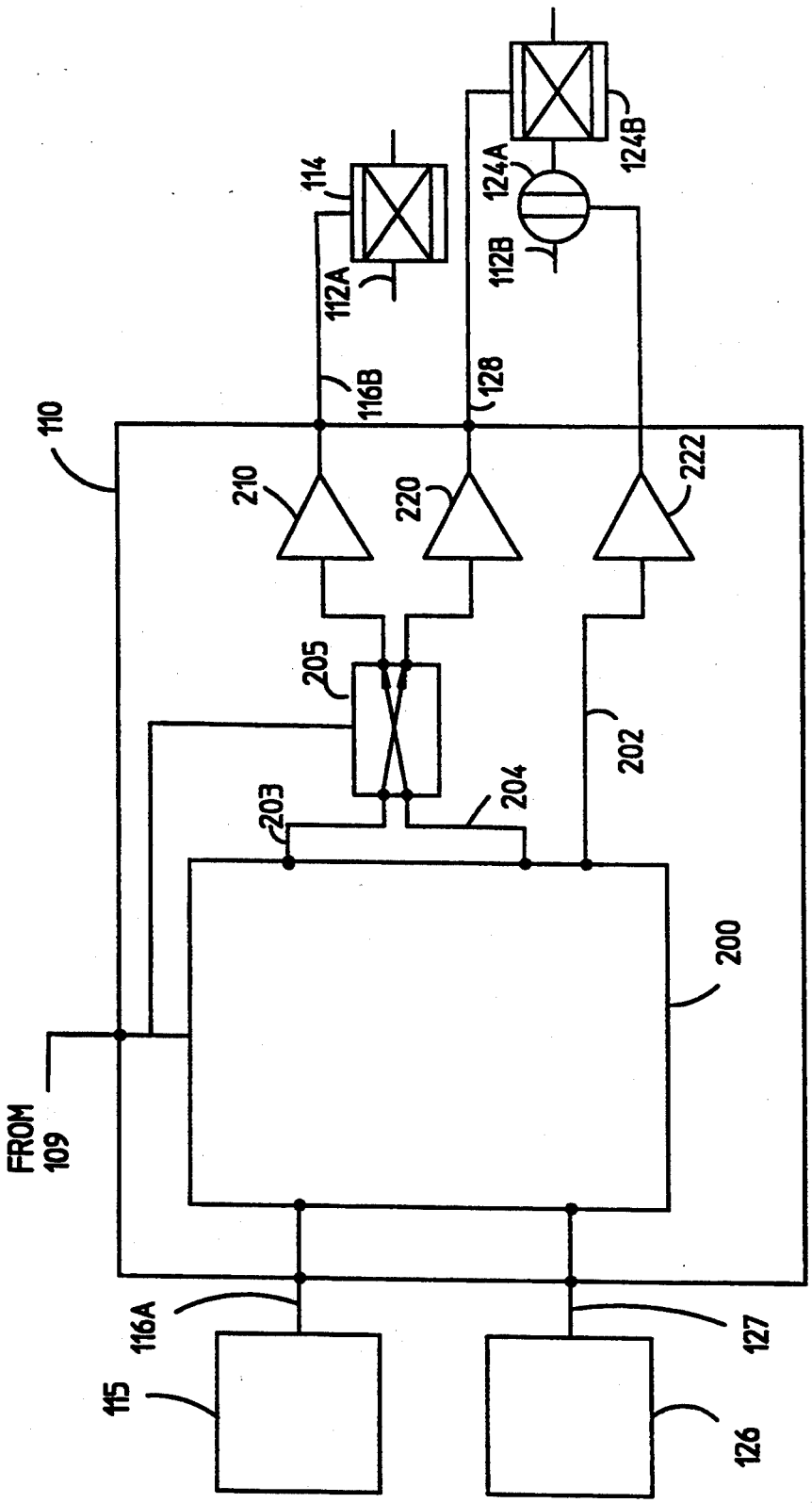
FIG. 4B is a simplified schematic representation of the preferred embodiment of FIG. 3A, during operation in a second mode preferred for splitless injection.
Figure 5:
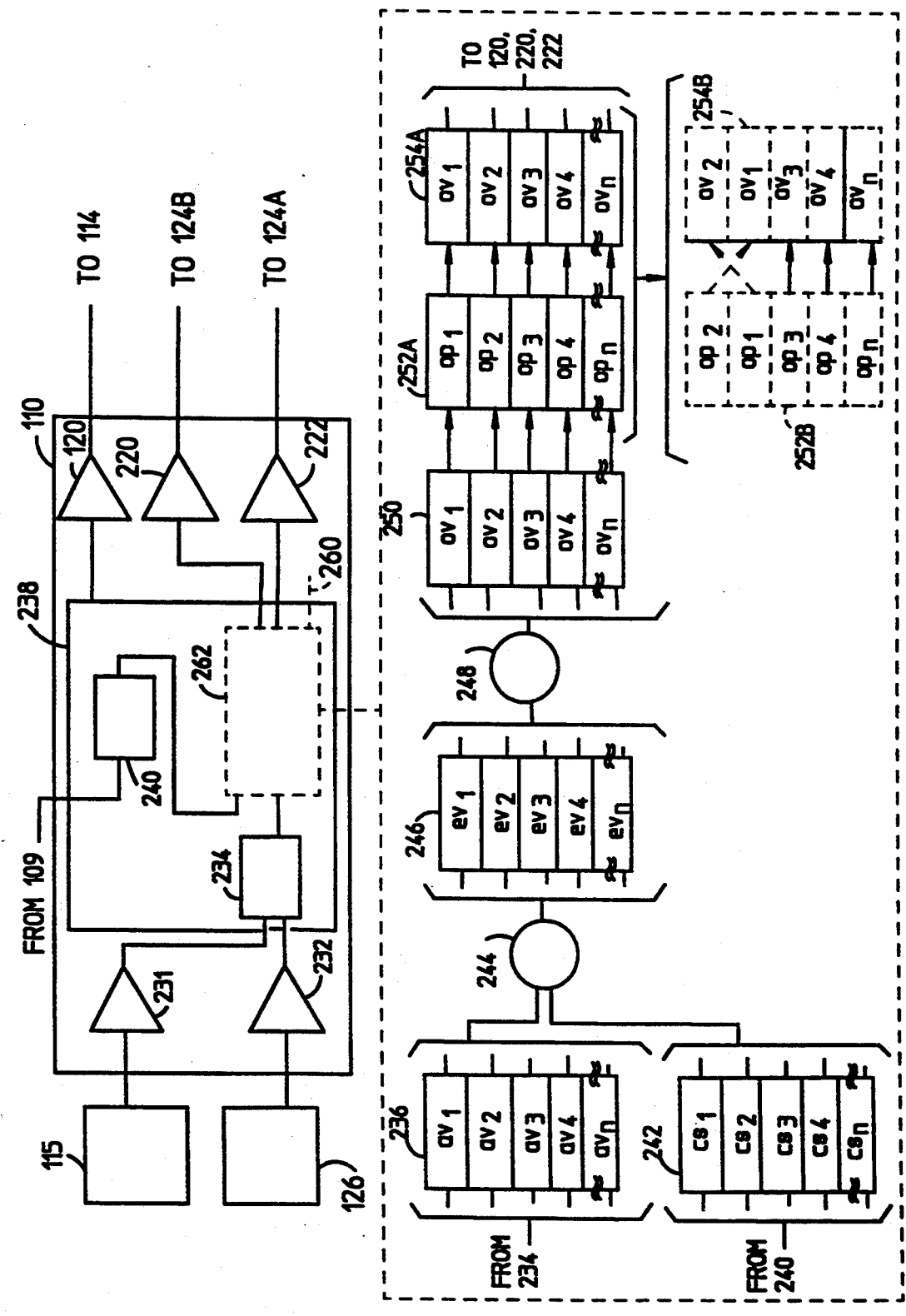
FIG. 5 is a simplified schematic representation of a particularly preferred embodiment of the fluid controller of FIG. 3A.

As shown in FIGS. 3–5, a gas chromatographic analysis system (100) may be constructed according to the present invention to include certain components already described with reference to FIGS. 1–2. Components of like nomenclature and reference numerals are intended to be equivalent.

Figure 3A:
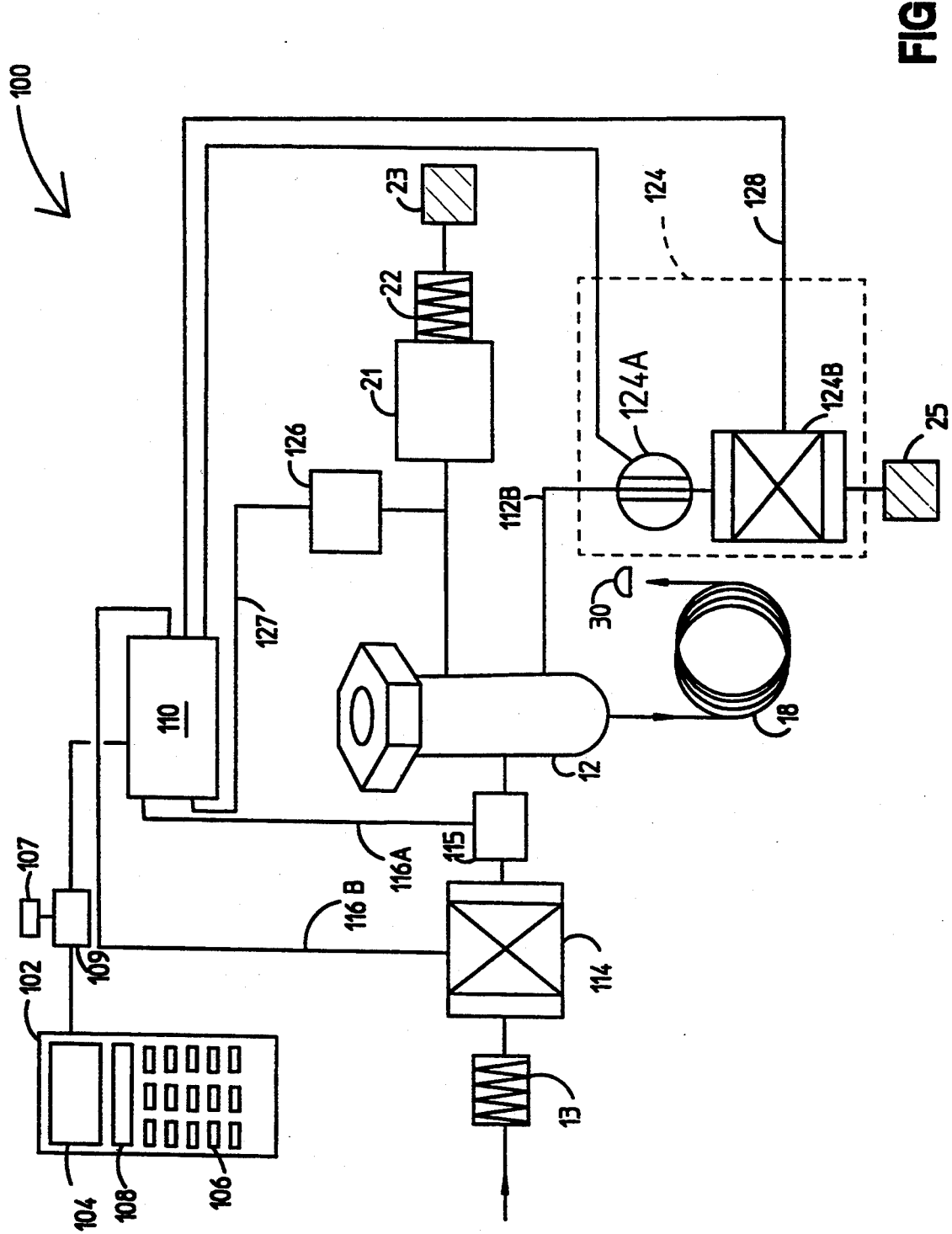
FIG. 3A is a simplified schematic representation of a preferred embodiment of a gas chromatographic analysis system constructed according to the present invention.

The preferred embodiment (100) of FIG. 3A is constructed as a keyboard-operated, table-driven gas chromatograph wherein the system configuration and operation, and particularly the operation of the gas streams for the unit's injection and detection systems, can be controlled by use of an input/output device (102) or via a communication line to a remote controller (107) such as a computer workstation, central control station, or another gas chromatograph. The operator may perform data entry and control table editing by way of a keyboard (106). A status board (108) displays information about the current status of certain systems while the chromatograph is in operation.

Figure 3B:
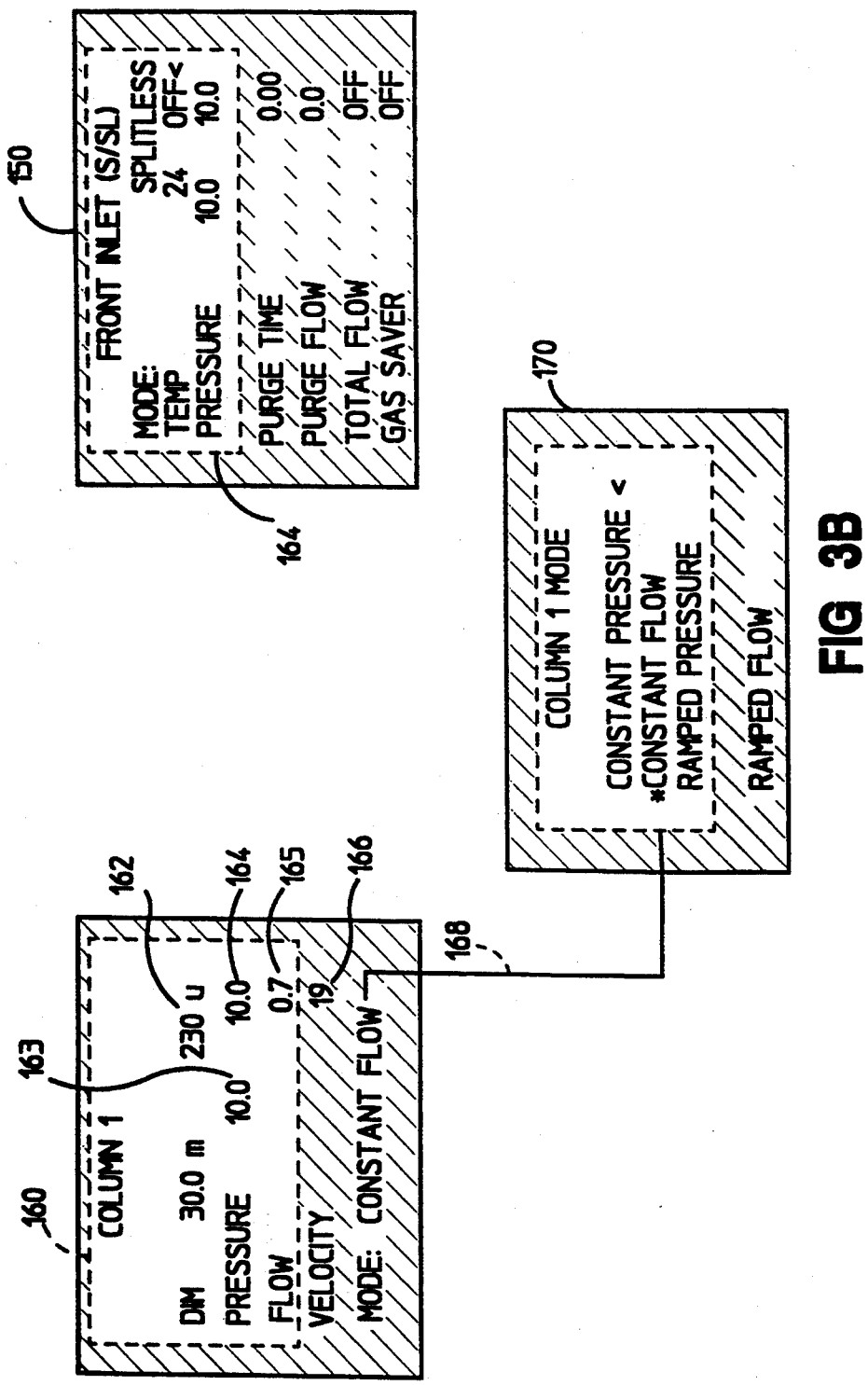
FIG. 3B is a graphical representation of some of the control tables used by the gas chromatographic analysis system of FIG. 3A.

Actual values of certain operating parameters, and system control values (also stated herein as setpoints), are organized into one or more control tables that are created in response to data from the remote controller (107) or (preferably) in response to data input by the operator on the input/output device (102) and to programming and firmware operative in a system controller (109). The tables are viewable and editable on a display (104). FIG. 3B illustrates examples of a few tables (inlet, column, and mode control tables (150, 160, 170)) as they would be rendered on the display (104). Examples of certain parameters of interest are: column dimensions (162), actual column pressure (163), column pressure setpoint (164), column flow rate (165), and calculated average linear velocity (166), and control mode (168).

The system controller (109) preferably includes data acquisition, memory, computation, and other process control circuitry suited for initiating and controlling the various functions relative to operation of the gas chromatograph (100), and software and/or firmware pertinent to carrying out the functions and operations indicated in the control tables, and in particular the generation, storage, and editing of the tables indicated on the display (104). The gas chromatograph (100) is preferably operable in split and splitless injection modes, with the latter including an optional pulsed splitless mode. An injection mode may be selected by use of the mode table (150) displayed on the input/output device (102). A pulsed splitless injection mode, for example, may include a pressure pulse feature, wherein the inlet pressure is increased at the beginning of an analysis and then is reduced to a normal level after selectable delay time.

In the preferred embodiment, regulated carrier gas flow, frit 13 and is provided via an inlet flow fluid controller, preferably in the form of a proportional control valve (114), to the split/splitless injection port (12). During a split injection mode, a sample is introduced into the heated inlet (12) where it vaporizes. A small amount of the sample/carrier gas mixture enters the column (18) while the majority of the sample/carrier gas mixture is vented out of the split vent (25). The split flow/column flow mixture ratio may be set by the operator according to the use of the input/output device (102) or remote controller (107) described above. In a splitless injection mode, a split line control valve (124) in the form of a bubble-tight shutoff valve (124A) and a proportional valve (124B) is closed during the injection and remains closed while the sample is vaporized and transferred to the column (18). At an operator-specified time after the injection, and the sample/carrier gas mixture has been received into the separation column (18), the split vent fluid controller is opened and any vapors remaining in the inlet are purged. Purge time and flow rate may be specified by editing the inlet control table (150).

Depending upon the injection mode and the control table setpoints in effect, flow may pass through a combination of a septum purge line (112A) or a split line (112B), or both. However, the conventional three-way purge valve (20) (in FIGS. 1-2) is omitted. Septum purge flow is directed to the septum purge controller (21), flow restrictor (22), and septum purge vent (23); split vent flow passes directly to the shutoff valve (124A) and proportional control valve (124B), and then to a split vent (25). In FIG. 3A, the shutoff valve (124A) is illustrated in the "open" (full flow) position; a "closed" (zero flow) position is optionally selectable, as will be described below.

With reference in particular to FIGS. 4-5, the preferred embodiment may be seen to include a reconfigurable fluid control system (110) having a setpoint controller (200) that receives a first sense signal from a first sensor (115) by way of sense line (116A). The first sensor (115) is preferably an inlet flow sensor that provides a sense signal representative of the inlet gas flow, and accordingly the setpoint controller (200) is implemented to provide a first setpoint control output value on output line (203). The setpoint controller (200) receives a second sense signal from a second sensor (126) by way of sense line (127). The second sensor (126) is preferably a gage pressure sensor that provides a sense signal representative of the pressure at a point in the septum purge line (112A), which is indirectly representative of the column head pressure at the head of the column (18). Accordingly the setpoint controller (200) is preferably implemented to provide a second setpoint control output value on output line (204).

As will now be described, the aforementioned first and second setpoint control output values are determined by the setpoint controller (200) according to pressure and flow control programming in response to one or more parameters and modes selected from the control tables. In the preferred embodiment, the selection criteria includes the injection mode (split, splitless, or pulsed splitless), and related conditions, such as the onset of an inlet purge during a splitless injection mode. However, it is contemplated that other criteria may be used. Further, the application of the setpoint control output values by the fluid control system (110) to the inlet control valve (114) and split line control valve (124) is selectably reconfigurable at any time in accordance with the control tables that are currently operative. Additionally, the fluid control system (110) interacts with the system controller (109) to send and receive other data and control signals. For example, actual values such as the actual inlet pressure, and setpoint values such as the column head pressure setpoint, may be provided to the system controller (109) for display on the input output device (102).

Each of the first and second setpoint control output values on respective lines (203, 204) from the setpoint controller (200) are actively directed by a configuration module (205) to a forward device driver (210) or back device driver (220). The forward device driver (210) converts the setpoint control output value that it has received to a control signal for use by the proportional control valve (114). The back device driver (220) converts the received setpoint control output value to a control signal for use by the proportional valve (124B). The fluid flow entering the injection port (12) on the inlet line is thereby controlled by the control valve (114) in response to a signal applied on the first control line (116B). The pressure of the carrier gas exiting the injection port (12) on the split line (112B) is thereby controlled by the split vent control valve (124) in response to a signal applied on a second control line (128). In the illustrated embodiment, wherein the shutoff valve (124A) is preferred to ensure bubble-tight closure of the proportional control valve (124B), a third setpoint control output value is selectably provided to a shutoff device driver (222) on line (202).

In FIG. 4A, the configuration module (205) is illustrated in a first configuration preferred for a split injection mode, wherein the first setpoint control output value is directed to the forward device driver (210) which drives the inlet control valve (114) to control the carrier gas inlet flow at the inlet (12), and the second setpoint control output value may be directed to the back device driver (220) to drive the split vent control valve (124). As the column head pressure at the head of the separation column (18) is directly related to the split vent pressure controlled by the split vent control valve (124), the column head pressure is thereby controlled. The third setpoint control output value is provided to the shutoff valve (124A) to fully open the shutoff valve.

In FIG. 4B, the configuration module (205) is illustrated in a second configuration preferred for splitless and pulsed splitless injection mode wherein the first setpoint control output value is directed to the back device driver (220) to drive the split vent proportional control valve (124B), and the second setpoint control output value is directed to the forward device driver (210) to control the septum purge line pressure, which is directly related to the column head pressure during splitless operation, and hence the column head pressure is thereby controlled. The third setpoint control output value is provided to the shutoff valve (124A) to ensure zero split flow.

A particular feature of the present invention is that the aforementioned modes, conditions, and configurations may be implemented and changed 'on-the-fly', that is, at a programmable time during the run of a chromatographic separation. It will be appreciated by those skilled in the art that FIGS. 4 and 5 show simplified schematic illustrations of closed loop control circuits; thus, the programmable fluid control system (110) is contemplated as being implemented by use of one or a combination of the following: analog hardware, digital hardware, digital memory, programmable software, and firmware.

Accordingly, FIG. 5 illustrates a particularly preferred embodiment wherein the setpoint controller (110) and configuration module (205) are implemented in the form of an embedded digital microprocessor operating memory arrays under the control of control firmware. Thus, analog to digital (A/D) converters (231,232) in combination with an actual value generator (234) provide actual values $av_1, av_2, \ldots av_n$ to an actual value array (236) maintained by a processor (238). Control table values and other data are received from the system controller (109) (of FIG. 3A) by a mode and setpoint generator (240), which then provides control setpoints $cs_1, cs_2, \ldots cs_n$ to a control setpoint array (242). A comparator algorithm (244) compares each actual value to its respective control setpoint and computes respective error values $ev_1, ev_2, \ldots ev_n$ for storage in an error value array (246). A proportional integral derivative (PID) algorithm (248) then computes respective controller output values $ov_1, ov_2, \ldots ov_n$ for storage in an output value array (250). A controller output pointer array (252A, or in the alternative, 252B) holds output pointers opt, op2, ...Opn. The output values $ov_1, ov_2, \ldots ov_n$ may thereby be directed to an output address array (254A, or in the alternative, 254B) according to the output pointers opt, $Op_2, \ldots Op_n$. As illustrated in the change from array (252A) to the array (252B), by changing the values of the output pointers, the output values may be reconfigured from a first arrangement $ov_1, ov_2, \ldots ov_n$ in the output address array (254A), to a second arrangement $ov_2, ov_1, \ldots ov_n$ in the reconfigured output address array (254B) illustrated in broken lines. In summary, the renumbering of the output pointers serves to redirect the location of the output values in the output address array.

Figure 1:
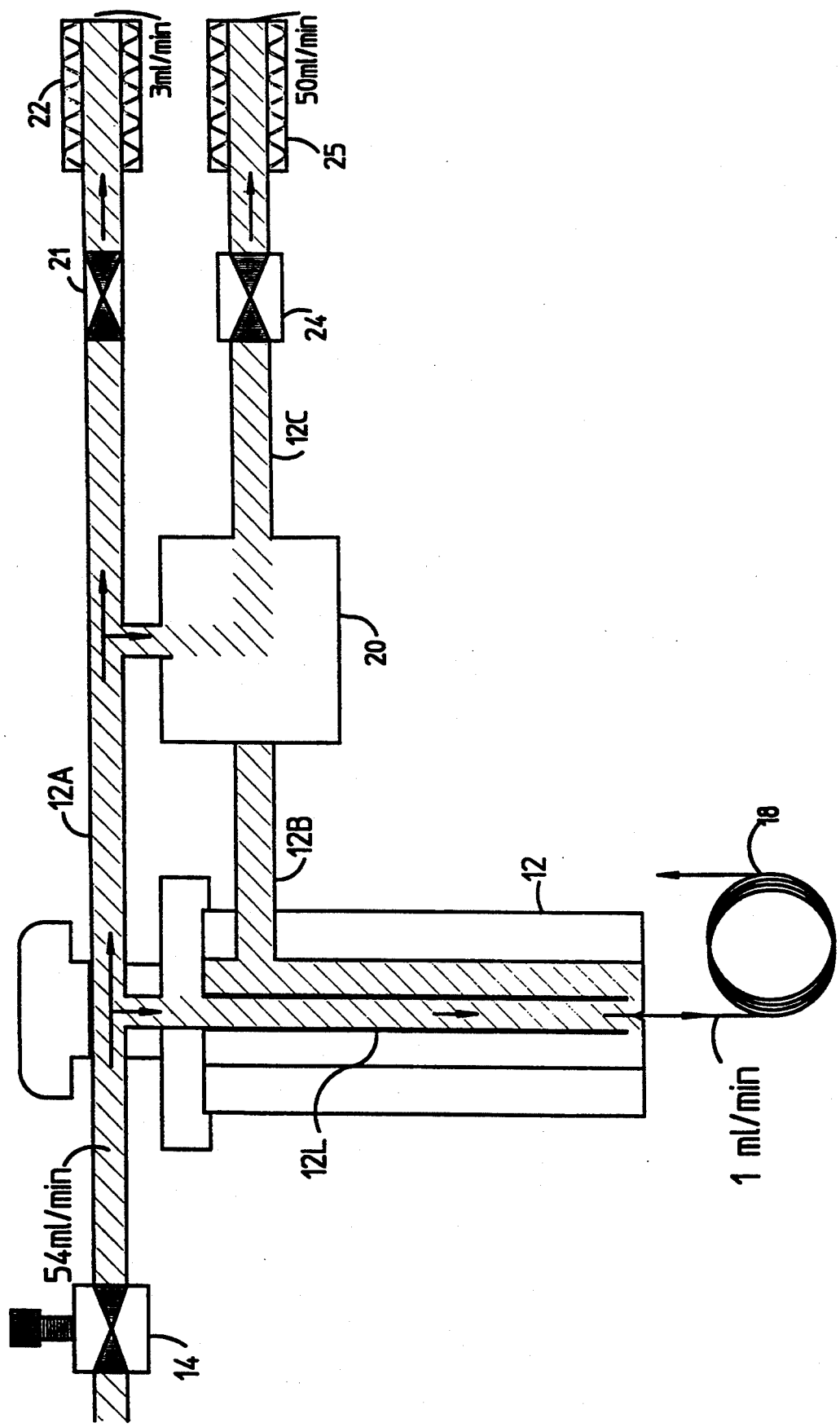
FIG. 1 is a simplified representation of the fluid flow in a conventional split/splitless inlet, during operation in a splitless injection mode, showing the purge "off" condition.
Figure 6A:
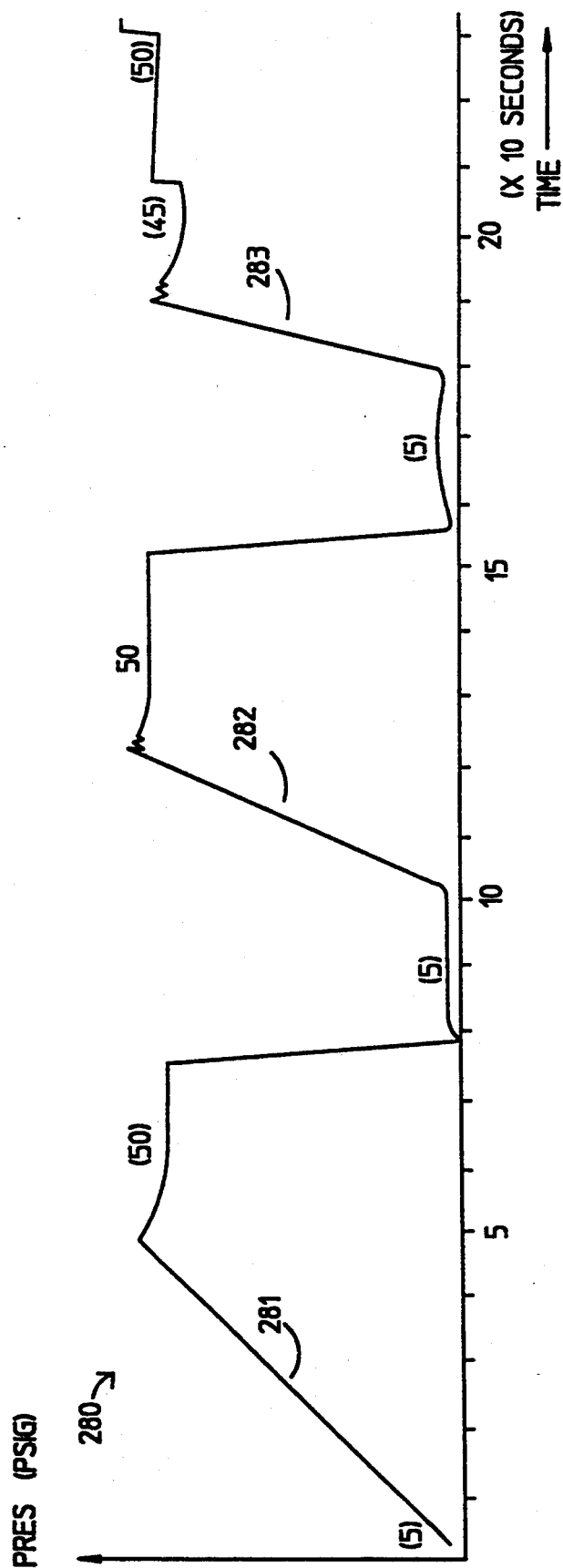
FIGS. 6A and 6B are graphical representations of the column head pressure and inlet carrier gas flow, respectively, in the system of FIG. 1.
Figure 6B:
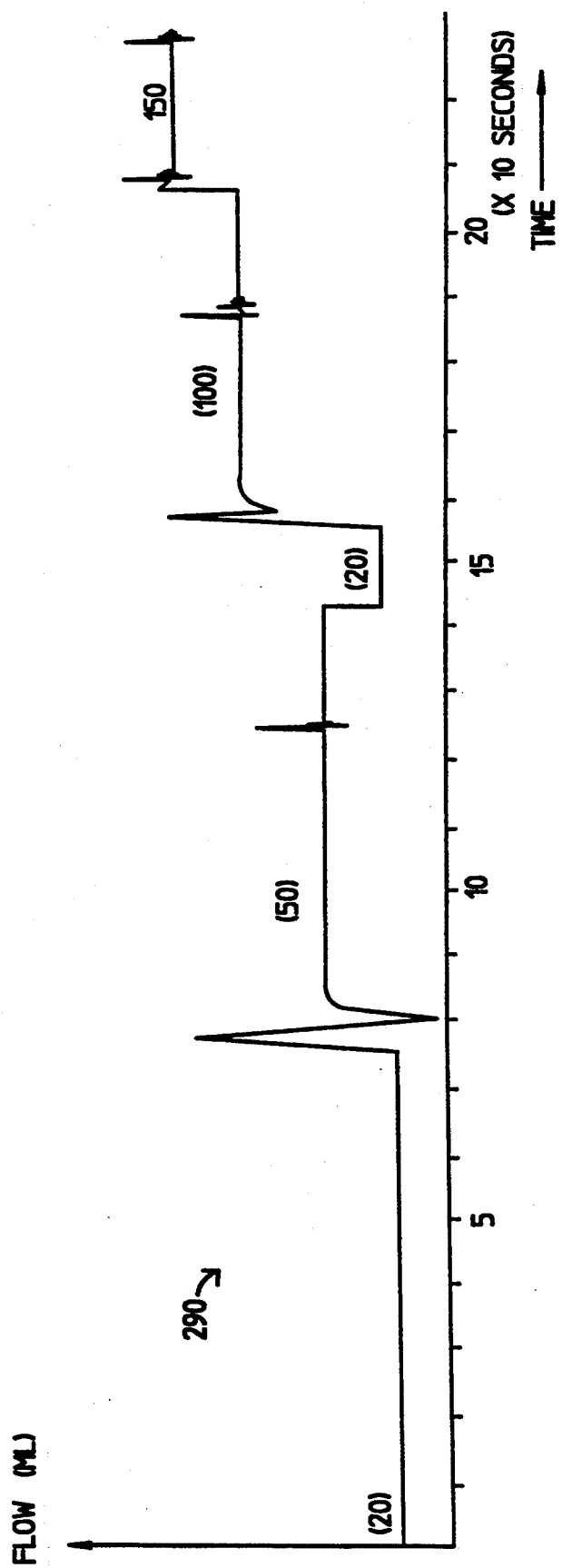

FIG. 6 is a graphical representation of the performance of a typical prior art gas chromatographic system having a split/splitless inlet such as that shown in FIG. 1, during back pressure regulation of the carrier gas flow. FIG. 6 illustrates the carrier gas pressure level (280) while inlet carrier gas flow (290) is provided to the inlet (12) at four typical carrier gas flow rates (20 ml/minute, 50 ml/minute, 100 ml/minute, and 150 ml/minute). As indicated by the column head pressure level ramps (281, 282, 283) that accompany the flow rates at 20 ml/sec, 50 ml/sec., and 100 ml/sec., respectively, the column head pressure increases relatively slowly at these low flow rates. As a result, a pressure pulse is quite slow to build at such flow rates, and a run of the apparatus will take more time to complete. With fewer runs per hour of operation, a laboratory that performs repeated analyses with such apparatus will achieve less "throughput".

Figure 7B:
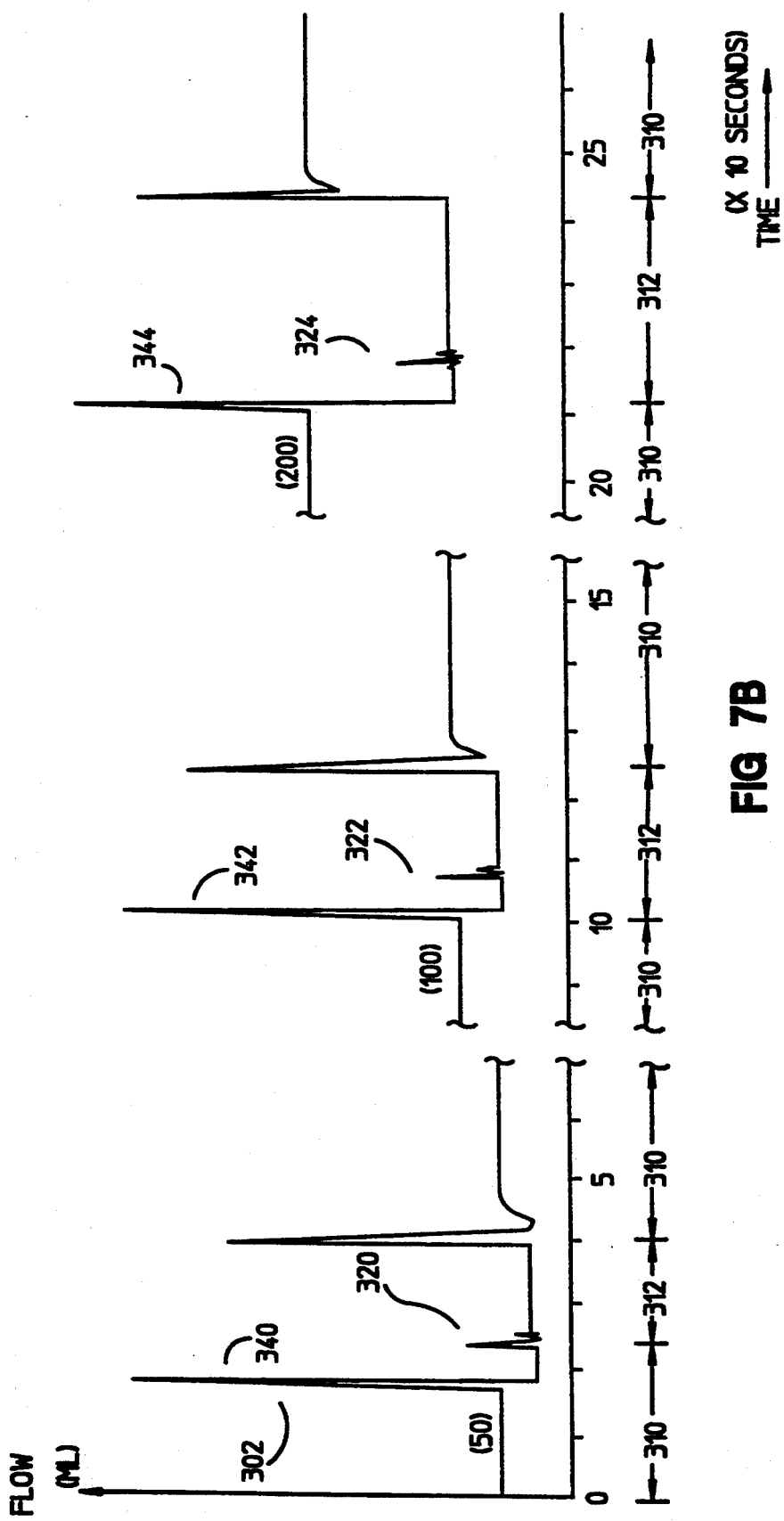

In contrast, FIG. 7 is a graphical representation of the performance of an experimental prototype of the preferred embodiment, such as shown in FIGS. 4 and 5, during alternating split (310) and splitless (312) modes of operation with forward pressure regulation of the carrier gas flow. FIG. 7 illustrates the column head pressure level (300) while carrier gas flow (302) at three experimental carrier gas flow rates (320, 322, 324) is provided to the inlet (12). FIG. 7 illustrates the column head pressure level ramps (330, 332, 334) that accompany inlet flow rates at 50 ml/sec, 100 ml/sec., and 200 ml/sec., respectively. FIG. 7 also shows the result of a reconfiguration of the pressure and flow setpoints during transitions from split (310) to splitless (312) modes, 15 wherein immediate pressure pulsing of the inlet may be effected. The pressure level changes will be recognized as being more rapid and stable across the transitions between modes. Column head pressure can be increased or decreased quite rapidly at the low flow rates of 50 ml/sec and 100 ml/sec. As a result, the desired pressure pulses (340, 342, 344) are successfully applied even at low flow rates.

The example listed below represents the performance of an experimental prototype of the preferred embodiment, such as shown in FIGS. 4 and 5, during alternating split (310) and splitless (312) injection modes of operation, in comparison to a conventional chromatographic system constructed according to the system (10) of FIG. 1. As is shown below, the experimental protype offers a performance improvement over prior art systems.

| EXAMPLE | |
| --- | --- |
| System Configuration | Description |
| 1. Auto/splt/Modified-EPC | Preferred embodiment with auto-sampler; operated in split mode; back pressure regulation |
| 2. Auto/spls/Modified-EPC | Preferred embodiment with auto-sampler; operated in splitless mode; forward pressure regulation |
| 3. Auto/PCOC/C-EPC | Conventional system with auto-sampler operated in cool-on column mode |
| 4. Manual/PCOC/C-EPC | Conventional system, manual injection, cool-on column inlet |
| 5. Auto/splt/Manual | Conventional system with auto-sampler, inlet operated in split mode, manual pressure control |

-continued

| System Configuration | Retention Time Standard Deviation Range (min) |
| --- | --- |
| 1. Auto/splt/Modified-EPC | 0.001–0.005 |
| 2. Auto/spls/Modified-EPC | 0.001–0.009 |
| 3. Auto/PCOC/C-EPC | 0.002–0.024 |
| 5. Auto/splt/Manual | 0.005–0.019 |

| System Configuration | Area Precision, % Range in Standard Deviation | Total Area |
| --- | --- | --- |
| 1. Auto/spls/Modified-EPC | 0.25–1.86 | 0.59 |
| 2. Auto/splt/Modified-EPC | 1.10–3.19 | 1.59 |
| 3. Auto/PCOC/C-EPC | 0.18–1.68 | 0.35 |
| 4. Man/PCOC/C-EPC | 1.97–7.82 | 3.42 |
| 5. Auto/splt/man | 1.15–4.47 | 2.26 |

Figure 2:
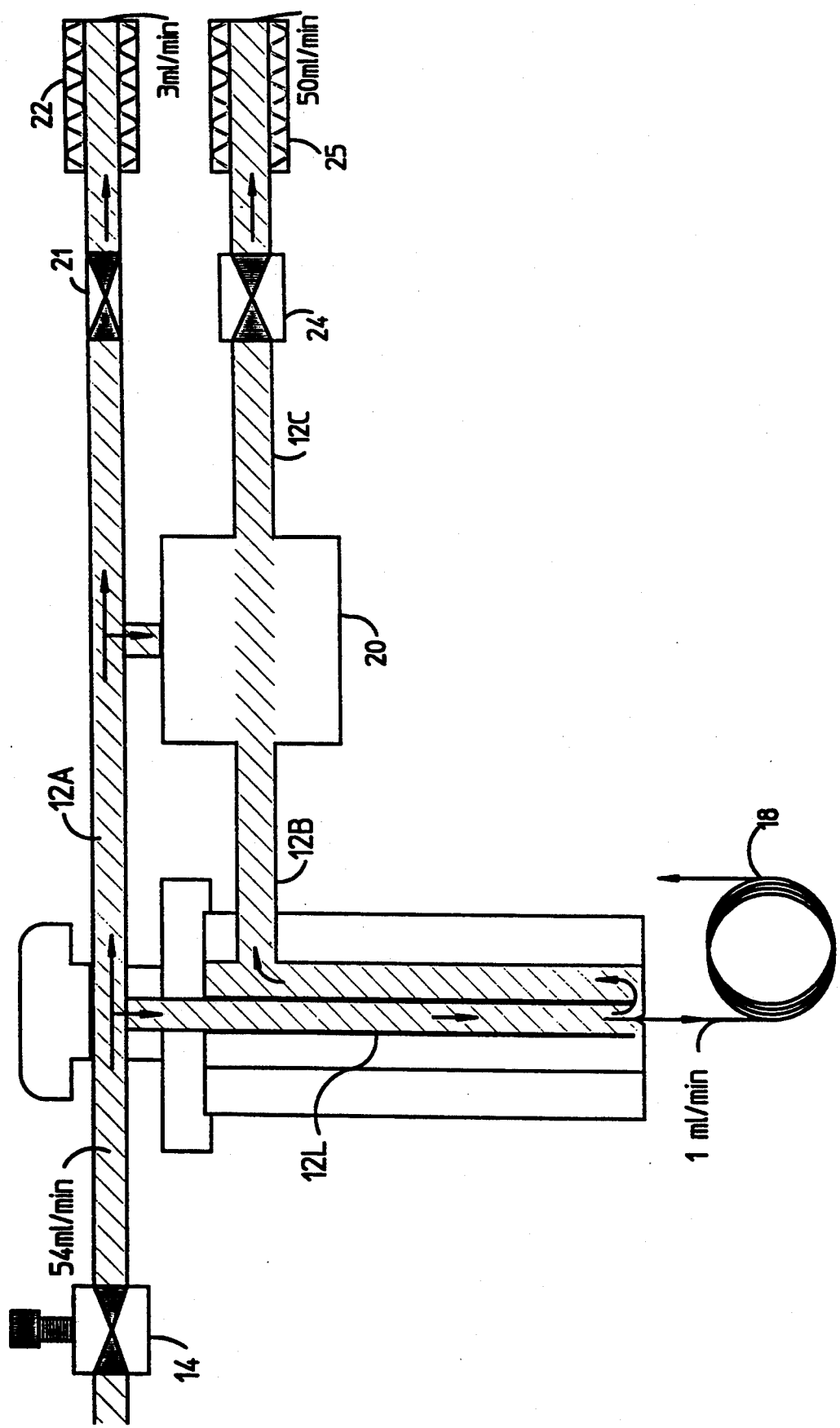
FIG. 2 is a simplified representation of the fluid flow in the split/splitless inlet of FIG. 1, during operation in a split injection mode, showing the purge "on" condition.

With respect to the prior art systems described with respect to FIGS. 1–2, the preferred embodiment illustrated in FIGS. 4–5 is particularly distinguished in that the setpoint controller (200) cooperates with the configuration module (205) such that setpoint control of the fluid control system (110) is reconfigurable in either of three injection modes (split, splitless, or pulsed splitless), with forward pressure regulation or back pressure regulation, wherein the modes and regulation are changeable at a programmable time during a run of the gas chromatograph.

Further, the requisite transitions in column head pressure between these injection modes are effected more rapidly. Pressure pulse programming may thus be implemented more quickly in the preferred embodiment than in the prior art. The flow and pressure setpoint control output values may be optimized for each of the split, splitless, and pulsed splitless injection modes, resulting in improved control of the column flow and more accurate sample analysis. Another benefit is that the septum purge flow setpoint may be reduced and area recovery is improved in comparison to the prior art, due in part to the lower septum purge flow that is less likely to draw sample from the top of the inlet (12).

The conventional three-way valve (20) and its associated components (not shown) are therefore unnecessary and thus are omitted. Because the stop valve (124A) is simpler and more reliable than the three way valve (20) of FIG. 1, the preferred embodiment is less costly and less subject to failure than a conventional system.

Although the invention has been described with reference to the above-described preferred embodiments, variations and modifications are contemplated as being within the scope and spirit of the present invention. For example, although only two of the output values are illustrated as being redirected in the output address array (254A to 254B), it is contemplated that any number of output values may be redirected. Moreover, certain ones of the output values may be provided from the output address array (254) to additional device drivers (not shown) on additional lines (indicated by the additional device driver line (260)). In certain applications of the present invention, the split vent fluid controller need not provide bubble-tight shutoff, and the controller thus may be in the form of a single valve (124B) operated according to a single setpoint control output value. Further, the forward and back device drivers (210, 220) may include additional digital to analog conversion devices and signal conditioning circuitry.

What is claimed is:

1. Method of performing a chromatographic separation of a sample, comprising the steps of:
   combining the sample and an inlet fluid to provide a mixture in an injection port, wherein the injection port includes an inlet line and a split vent line for passing respectively an inlet fluid flow and a split vent fluid flow;
   providing at least a portion of the mixture to a separation column in a column fluid flow;
   providing sense information representative of the fluid flow in the inlet line and the column head pressure;
   determining control table information representative of a selected one of split and splitless injection modes and a selected one of forward and back pressure regulation modes;
   determining first and second setpoint control output values, in accordance with the sense information and the control table information;
   providing a first regulation of the inlet fluid flow;
   providing a second regulation of the split vent fluid flow;
   when the injection port is operated in a split injection mode, effecting the first and second regulations according to the first and second setpoints, respectively, to provide inlet fluid flow control and back pressure regulation of the column head pressure; and
   when the injection port is operated in a splitless injection mode, effecting the first and second regulations according to the second and the first setpoints, respectively, to provide forward pressure regulation of the column head pressure.

2. Apparatus for performing a chromatographic separation of a sample, comprising:
   an injection port having an inlet therein for combining the sample and an inlet fluid and for providing a column fluid flow to a separation column, wherein the injection port includes an inlet line and a split line for passing respectively an inlet fluid flow and a split fluid flow;
   sense means for providing sense information representative of the fluid flow in the inlet line and the fluid pressure in the separation column;
   a system controller for providing control table information representative of a selected one of split and splitless injection modes and a selected one of forward and back pressure regulation modes;
   a first control valve operatively connected to the inlet line;
   a second control valve operatively connected to the split line; and
   a reconfigurable fluid control system having:
   a) a setpoint controller for determining first and second setpoint control output values, in accordance with the sense information and the control table information, and
   b) a configuration module for controlling the first and second control valves according to the first and second setpoint control output values, respectively, when the injection port is operated in a split injection mode, and for controlling the second and first control values according to the first and second setpoint control output values, respectively, when the injection port is operated in a splitless injection mode.

3. The apparatus of claim 2, wherein the first and second setpoint control values effect back pressure regulation of the split mode injection.

4. The apparatus of claim 2, wherein the first and second setpoint control values effect forward pressure regulation of the splitless mode injection.

5. The apparatus of claim 2, wherein the reconfigurable fluid control system includes program control to provide a pulsed splitless mode injection.

6. The apparatus of claim 2, wherein the fluid control system further comprises:
- a shutoff valve, operatively connected to the split line;
- a forward device driver, responsive to the first setpoint control value,
- a back device driver, responsive to the second setpoint control value,
- a shutoff device driver, responsive to a third setpoint control value, wherein the forward device driver is operatively connected to the first control valve of controlling fluid flow in the inlet line, and the second control valve and shutoff valve operatively connected to the back device driver and shutoff device driver, respectively, for effecting control of the fluid pressure in the split line.

7. The apparatus of claim 2, further comprising an input/output device for receiving input data and for displaying control table information pertinent to the operation of the system controller.

8. The apparatus of claim 2, wherein the reconfigurable fluid control system further comprises:
- an actual value array for storage and retrieval of plural actual values $av_1, av_2, \ldots av_n$ representative of selected system operating parameters;
- a mode and setpoint generator for providing plural control setpoints $cs_1, cs_2, \ldots cs_n$ representative of selected control table values;
- a control setpoint array for storage and retrieval of the control setpoints;
- a comparator algorithm for comparing each actual value to its respective control setpoint and computing plural respective error values $ev_1, ev_2, \ldots ev_n$;
- an error value array for storage and retrieval of the computed error values;
- an algorithm for computing a plurality of respective controller output values $ov_1, ov_2, \ldots ov_n$;
- an output value array for storage and retrieval of the controller output values;
- a controller output pointer array for storage and retrieval of a plurality of output pointers $op_1, op_2, \ldots op_n$; and
- an output address array for receiving the output values $ov_1, ov_2, \ldots ov_n$ from the output value array according to the output pointers $op_1, op_2, \ldots op_n$;
- wherein the values of the output pointers are programmable to reconfigure the output values in the output address array from a first order of values to a second order of values.

9. The apparatus of claim 2, wherein the first and second setpoint control values effect flow control of the inlet fluid flow.

10. An apparatus for performing a chromatographic separation of a sample, comprising:
- an injection port having an inlet therein for combining the sample and an inlet fluid and for providing a column fluid flow to a separation column, wherein the injection port includes an inlet line and a split line for passing respectively an inlet fluid flow and a split fluid flow;
- a first sensor for providing a respective sense signal representative of the fluid flow in the inlet line,
- a second sensor for providing a respective sense signal representative of the fluid pressure in the separation column;
- a system controller for providing control table information;
- a reconfigurable fluid control System, comprising:
- a setpoint controller for receiving the first and second sense signals and the control table information and accordingly determining first and second setpoint control output values;
- a forward device driver operatively connected to a first control valve for controlling fluid flow in the inlet line;
- a back device driver operatively connected to a second control valve for controlling fluid pressure in the separation column; and
- a configuration module operatively connected to the setpoint controller for selectably providing the first and second setpoints to the forward and back device drivers when the injection port is operated in a split injection mode and providing the second and first setpoints to the forward and back device drivers respectively, when the injection port is operated in a splitless injection mode.

* * * * *